(12) United States Patent
Curstedt et al.

(10) Patent No.: US 7,053,044 B1
(45) Date of Patent: May 30, 2006

(54) ARTIFICIAL PEPTIDES HAVING SURFACE ACTIVITY AND THE USE THEREOF IN THE PREPARATION OF ARTIFICIAL SURFACTANT

(75) Inventors: Tore Curstedt, Parma (IT); Jan Johansson, Parma (IT); Hans Jörnvall, Parma (IT); Paolo Ventura, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/926,009

(22) PCT Filed: Feb. 9, 2000

(86) PCT No.: PCT/EP00/01044

§ 371 (c)(1),
(2), (4) Date: Dec. 11, 2001

(87) PCT Pub. No.: WO00/47623

PCT Pub. Date: Aug. 17, 2000

(30) Foreign Application Priority Data

Dec. 2, 1999 (IT) .............................. MI99A0275

(51) Int. Cl.
*A61K 38/00* (2006.01)

(52) U.S. Cl. .............................. 514/2; 514/13; 530/326
(58) Field of Classification Search .................... 514/2, 514/13; 530/326
See application file for complete search history.

(56) References Cited

FOREIGN PATENT DOCUMENTS

| EP | 0 368 823 | 5/1990 |
| EP | 0 733 645 A1 | 9/1996 |
| WO | WO 91/18015 | 11/1991 |

OTHER PUBLICATIONS

Palmblad et al. "Biophysical activity of an artifical surfactant containing an analogue of surfactant protein (SP)-C and native SP B" 1999, Biochem J. 339(2) pp 381-386.*
Marie Palamblad, et al., Biophysical activity of an artificial surfactant containing an analogue of surfactant protein (SP)-C and native SP-B, Biochemical Journal, vol. 339, pp. 381-386, 1999.
Tsunetomo Takei, et al., The Surface Properties of Chemically Synthesized Peptides Analogous to Human Pulmonary Surfactant Protein SP-C, Biol. Pharm. Bull. vol. 19, pp. 1247-1253, 1996.
U.S. Appl. No. 10/512,869, filed Nov. 16, 2004, Curstedt, et al.
U.S. Appl. No. 09/926,009, filed Oct. 3, 2001, Curstedt, et al.

* cited by examiner

*Primary Examiner*—Christopher Tate
*Assistant Examiner*—Roy Teller
(74) *Attorney, Agent, or Firm*—Oblon, Spivak, McClelland, Maier & Neustadt, P.C.

(57) ABSTRACT

SP-C analogue artificial peptides having surface activity are disclosed and their use for preparing artificial surfactants useful in the treatment of respiratory distress syndrome (RDS) and other diseases related to surfactant deficiency or dysfunction.

31 Claims, 3 Drawing Sheets

```
Human SP-C      FGIPCCPVHLKRLLIVVVVVVLIVVVIVGALLMGL
SP-C(Leu)       ----SS--A------LLLLLL--LLL-L-------
SP-C[LKS]       ----SS---------LKLLLK-LLKL--------
```

ARTIFICIAL PEPTIDES HAVING SURFACE ACTIVITY AND THE USE THEREOF IN THE PREPARATION OF ARTIFICIAL SURFACTANT

The present invention provides new artificial peptides having surface activity. In particular, the invention provides SP-C analogues which, once combined with suitable lipids, are particularly effective in reducing surface tension at the air-liquid interface.

Thus, the peptides of the invention may be used in combination with lipids, and optionally in combination with SP-B or an active analogue thereof or a substitute of SP-B, for preparing artificial surfactants useful in the treatment of respiratory distress syndrome (RDS), other surfactant deficiencies or dysfunction, related pulmonary diseases such as pneumonia, bronchitis, asthma, meconium aspiration syndrome and also other diseases such as serous otitis media (glue ear).

BACKGROUND OF THE INVENTION

Pulmonary surfactant reduces surface tension at the air-liquid interface of the alveolar lining, preventing the lungs from collapsing at end expiration. Surfactant deficiency is a common disorder in premature infants and causes respiratory distress syndrome (RDS), which can be effectively treated with natural surfactants extracted from animal lungs (Fujiwara, T. and Robertson B. (1992) In: Robertson, B., van Golde, L. M. G. and Batenburg, B. (eds) Pulmonary Surfactant: From Molecular Biology to Clinical Practice Amsterdam, Elsevier, pp. 561–592). The main constituents of these surfactant preparations are phospholipids such as 1,2-dipalmitoyl-sn-glycero-3-phosphocholine (DPPC), phosphatidylgly-cerol (PG) and the hydrophobic surfactant proteins B and C (SP-B and SP-C). The hydrophilic surfactant proteins SP-A and SP-D which are C-type ($Ca^{2+}$-dependent) collagenous lectins and thought to act primarily in the host-defence system, are normally not included in the surfactant preparations due to the organic solvent extraction procedures employed.

SP-B and SP-C constitute only about 1–2% of the surfactant mass, but are still able to exercise dramatic improvements on surface activity, compared to pure lipid preparations (Curstedt, T. et al. (1987) Eur. J. Biochem. 168, 255–262; Takahashi, A., Nemoto, T. and Fujiwara, T. (1994) Acta Paediatr. Jap. 36, 613–618). The primary and secondary structures of SP-B and SP-C and a tertiary structure of SP-C in solution have been determined (see 4). SP-B is composed of two identical polypeptide chains of 79 amino acids, connected with an interchain disulphide bridge (Curstedt, T. et al. (1990) Proc. Natl. Acad. Sci. U.S.A. 87, 2985–2989; Johansson, J., Curstedt, T. and Jörnvall, H. (1991) Biochemistry 30, 6917–6921). Each monomeric chain has three intrachain disulphide bridges and at least four amphipathic helices exhibiting one polar and one unpolar face through which SP-B may interact with two lipid bilayers and bring them into close proximity (Andersson, M. et al. (1995) FEBS Lett. 362, 328–332). SP-C is a lipoprotein composed of 35 amino acid residues with an α-helical domain between residues 9–34 (Johansson, J. et al. (1994) Biochemistry 33, 6015–6023). The helix is composed mostly of valyl-residues and is embedded in a lipid bilayer and oriented in parallel with the lipid acyl chains (Vandenbussche, et al. (1992) Eur. J. Biochem. 203, 201–209). Two palmitoyl groups are covalently linked to cysteine residues in positions 5 and 6 in the N-terminal part of the peptide (Curstedt, T. et al. (1990) Proc. Natl. Acad. Sci. U.S.A. 87, 2985–2989). The two conserved positively charged residues, arginine and lysine, at positions 11 and 12, possibly interact with the negatively charged head groups of the lipid membrane, thus increasing its rigidity. The rigidity of the lipid-peptide interaction may be decreased towards the C-terminal end, since it contains small or hydrophobic residues only, making this part potentially more mobile in a phospholipid bilayer. SP-C is thought to influence the thickness and fluidity of the surrounding lipids via the extremely stable poly-valyl helix (Johansson, J. and Curstedt, T. (1997) Eur. J. Biochem. 244, 675–693).

STATE OF THE ART

Since surfactant preparations obtained from animal tissue present some drawbacks, like their availability in limited amounts and the possibilities that they contain infectious agents and induce immunological reactions, attempts have been made to create artificial surfactants (Johansson, J. and Curstedt, T. (1997) Eur. J. Biochem. 244, 675–693; Johansson, J. et al. (1996) Acta Paediatr. 85, 642–646), usually from synthetic lipids and hydrophobic proteins.

Previous work has demonstrated that synthetic SP-C may not fold like the native peptide into an α-helical conformation necessary for optimal surface activity (Johansson, J. et al. (1995) Biochem. J. 307, 535–541), and therefore do not interact properly with the surfactant lipids.

Consequently, synthetic SP-C analogues do not fold like the native peptide and do not interact properly with the surfactant lipids. To circumvent this problem, several attempts have been made to modify the sequence, for instance by replacing all helical Val residues in native SP-C with Leu, which strongly favour α-helical conformation. The corresponding transmembranous analogue, SP-C(Leu) showed good spreading at an air-liquid interface when combined with DPPC:PG:PA (68:22:9) (w/w/w). However, the maximum surface tension value during cyclic surface compression ($\gamma_{max}$) was significantly higher than that of native surfactant. It was furthermore not possible to prepare lipid-peptide mixtures of higher concentrations than about 20 mg/ml, probably due to formation of peptide oligomers (Nilsson, G. et al. (1998) Eur. J. Biochem. 255, 116–124). Others have synthesised bioactive polyleucine SP-C analogues of different lengths (Takei, T. et al. (1996) Biol. Pharm. Bull. 19, 1550–1555). In the latter studies neither self oligomerisation nor problems in producing samples of high lipid concentration were reported.

Different publications deal with the problem of providing peptidic analogues of natural surfactant peptides, giving a number of different solutions. Among those publications, WO93 21225, EP 733 645, WO96 17872, in the name of Tokyo Tanabe, disclose peptides analogues of natural SP-C, which in general differ from the native peptide regarding the sequence of the N-terminal part.

Scripps Research Institute patent applications WO89 06657 and WO92 22315 disclose SP-B analogues having alternating hydrophobic and hydrophilic amino acid residues. Among others, a peptide alternating Leucine and lysine residues ($KL_4$) is claimed.

Clercx A. et al., Eur. J. Biochem 229, 465–72, 1995, disclose peptides of different lengths corresponding to the N-terminal of porcine SP-C and hybrid peptides derived from porcine SP-C and bacteriorhodopsin.

Johansson J. et al., Biochem. J. 307, 535:41, 1995, disclose synthetic peptides that differ from the native porcine SP-C by the substitution of some amino acids.

WO89/04326 in the name of California Biotechnology—Byk Gulden, and WO91/18015 in the name of California Biotechnology—Scios Nova, disclose SP-C analogues containing an initial N-terminal sequence in which the two Cys of natural SP-C are replaced by two Ser.

DESCRIPTION OF THE INVENTION

It has now been found that SP-C analogue peptides which combine the following features: i) substitution of Val residues with other neutral and hydrophobic residues; ii) substitution of Cys residues with Ser residues; iii) replacement of some of the neutral amino acid residues with bulky or polar residues, show particularly favourable properties for surface tension reduction. In particular it has been found that the latter feature, in virtue of the positive charges conferred by the polar residues or the steric hindrance conferred by the bulky substituents, allow to avoid self-oligomerisation.

As follows, according to a first aspect, the invention provides SP-C analogues having the following general formula (I) SEQ ID NO:1, using the one-letter amino acid code:

$$F_e G_f IPZZPVHLKR(X_a B)_n (X_b B)_n (X_c B)_m X_d GALL\text{-}MGL \quad (I)$$

wherein:
X is an amino acid selected from the group consisting of V, I, L, Nle (norleucine);
B is an amino acid selected from the group consisting of Ornithine, K, I, W, F, Y, Q, N;
Z is an amino acid selected from the group consisting of S, C, F where Ser or Cys residues are optionally linked via ester or thio-ester bonds with acyl groups containing 12–22 carbon atoms linked.
a is an integer from 1 to 19
b is an integer from 1 to 19
c is an integer from 1 to 21
d is an integer from 0 to 20
e is 0 or 1
f is 0 or 1
n is 0 or 1
m is 0 or 1
with the conditions:
n+m>0,
f≧e;
$(X_a B)_n (X_b B)_n (X_c B)_m X_d$ is a sequence having a maximum of 22 amino acids, preferably from 10 to 22.

Preferred peptides of Formula (I) have the following sequences:

(Ia) FGIPSSPVHLKRX$_4$BX$_4$BX$_4$BXGALLMGL (SEQ ID NO:2)
(Ib) FGIPSSPVHLKRX$_5$BX$_5$BX$_4$GALLMGL (SEQ ID NO:3)
(Ic) FGIPSSPVHLKRX$_4$BX$_{11}$GALLMGL (SEQ ID NO:4)
(Id) FGIPSSPVHLKRX$_8$BX$_7$GALLMGL (SEQ ID NO:5)
(Ie) FGIPSSPVHLKRX$_{11}$BX$_4$GALLMGL (SEQ ID NO:6)

Among the sequences (Ia)–(Ie), those having B=Lys or Phe and X=Leu, Ile or Nle are preferred.

According to preferred embodiments, peptides of formula (Ia)–(If) have the following sequences, respectively:

FGIPSSPVHLKRLLILKLLLLKILLLKLGALLMGL
  [SP-C (LKS)] (SEQ ID NO:7)
FGIPSSPVHLKRLLILLKLLLLIKLLILGALLMGL
  [SP-C (LKS)$_1$] (SEQ ID NO:8)
FGIPSSPVHLKRLLILKLLLLLILLLILGALLMGL
  [SP-C (LKS)$_2$] (SEQ ID NO:9)
FGIPSSPVHLKRLLILLLLLLKLILLILGALLMGL
  [SP-C (LKS)$_3$] (SEQ ID NO:10)
FGIPSSPVHLKRLLILLLLLLLIKLLILGALLMGL
  [SP-C (LKS)$_4$] (SEQ ID NO:11)
FGIPSSPVHLKRLLILFLLLLFILLLFLGALLMGL
  [SP-C (LFS)] (SEQ ID NO:12)

In a more preferred embodiment of the invention, the Ser residues are covalently linked with acyl groups containing 12–22 carbon atoms.

Peptides of formula (I) may be prepared by synthetic methods or recombinant techniques.

Conventional synthetic methods are described, for instance, in Schroeder et al., "The peptides", vol. 1, Academic Press, 1965; Bodanszky et al., "Peptide synthesis", Interscience Publisher, 1996; Baramy & Merrifield, "The peptides; Analysis, Synthesis, Biology", vol. 2, chapter 1, Academic Press, 1980. Said techniques include peptide synthesis in solid phase, in solution, organic chemistry synthetic methods, or any combination thereof.

S- or O-acylated peptides are preferably synthesized by treatment of the non-acylated peptides with acyl chloride in neat trifluoroacetic acid as described in Yousefi-Salakdeh et al. Biochem J 1999, 343, 557–562. After synthesis and purification, the synthetic peptides were biochemically and biophysically characterised, as reported in the following section "Examples".

The activity of the peptides of the invention in reducing surface tension has been evaluated in combination with lipids and phospholipids, SP-B, analogues of SP-B or substitutes of SP-B. In particular, the peptides have been combined with DPPC (1,2-dipalmitoyl-sn-glycero-3-phosphocholine)/PG (phosphatidylglyce-rol)/PA (palmitic acid) with or without SP-B, an active analogue thereof and polymyxins.

The results of pulsating-bubble surface activity tests clearly show that the synthetic peptides according to the present invention strongly decrease minimum and maximum surface tension during cyclic surface compression ($\gamma_{min}$ and $\gamma_{max}$) to values comparable with those obtained using surfactants from natural sources.

The addition of SP-B or active analogue thereof to the mixture peptide/lipids-phospholipids gave particularly favourable results. Furthermore it has been surprisingly found that polymyxins, in particular polymyxin B, act as substitutes of SP-B and their addition gave comparable results to those achieved with SP-B.

According to a second aspect, the invention provides a synthetic surfactant comprising one or more peptides of formula (I), in admixture with lipids and/or phospholipids and optionally SP-B, an active derivative thereof or polymyxins. Suitable lipids/phospholipids may be selected from the group consisting of phosphatidylcholines (preferably DPPC) PG, PA, triacylglycerols, sphingomyelin.

In an even more preferred embodiment of the invention, surfactant mixtures containing the peptide in which palmitoyl chains are O-covalently linked to the Ser residues should be used. It has been found that surfactant mixtures containing a dipalmitoylated form of the reference peptide (SP-C(Leu)) exhibit higher surface film stability and increased size of the surface-associated lipid reservoir, compared to mixtures containing the corresponding non-palmitoylated peptide, as measured by captive bubble system. In the samples containing 5% of dipalmitoylated peptide, the $\gamma_{min}$ was below 1.5 mN/m and the films very stable, as the surface tension increased by less than 0.5 mN/m within 10 min at constant bubble volume. On the contrary, the $\gamma_{min}$ for the non-palmitoylated peptide was approx. 5 mN/m and the films were less stable as observed by frequent bubble clicking at low surface tensions. Moreover, after subphase depletion for samples that contain non-palmitoylated peptide, the ability to reach near zero stable surface tension was lost after a few adsorption steps, whereas with the dipalmitoylated peptide the film quality did not deteriorate even after more than 10 expansion steps and the incorporation of reservoir material equivalent to more than two monolayers. The improved surface activity of dipalmitoylated peptides was also demonstrated by pulsating bubble surfactometer. In addition, the presence of acyl groups was found to further reduce the tendency to form oligomers. This finding is very important, as during preparation of artificial surfactants, peptide oligomerisation has been found to hinder preparation of the mixtures at higher concentrations than 20 mg/ml (Nilsson et al. Eur J Biochem 1998, 255, 116–124).

The synthetic surfactant may be prepared by mixing solutions or suspensions of peptides and lipids and by subsequently drying the mixture.

At the occurrence, the dry mixture may be suspended, dispersed or administered as such to subjects in need of treatment for surfactant deficiency.

The synthetic surfactant will be preferably administered endotracheally or via aerosol. The latter form of administration will require the combination of small particles of surfactant with suitable inert propellant. Other forms of administration, like nebulization or spraying of stable solutions/suspensions of surfactant are also included within the scope of the invention.

According to a further aspect, the invention provides the use of the described peptides for the preparation of a surfactant agent to be used in all cases of adult or neonatal surfactant deficiency or dysfunction, related pulmonary diseases such as pneumonia, bronchitis, asthma, meconium aspiration syndrome and also other diseases such as serous otitis media (glue ear).

Typically, the surfactant agent will be used, preferably upon endotracheal administration, in the treatment of respiratory distress syndrome which frequently affects premature infants.

The following examples illustrate the invention in more details.

EXAMPLE 1

Peptide Synthesis and Purification

An analogue of SP-C, SP-C(LKS) (FIG. 1) was synthesised by use of stepwise solid phase technology and the tert-butyloxycarbonyl chemistry (Kent, S. B. H. (1988) Annu. Rev. Biochem. 57, 957–989) in an Applied Biosystems 430A instrument. Cleavage of the resin-peptide bond and deprotection of the side-chains were carried out in anhydrous hydrogen fluoride/metoxybenzene/dimethylsulfide, 10:1:1 (v/v/v) for 1.5 h at 0° C. Protecting groups and scavengers were removed by repeated extraction with diethyl ether and the peptide was subsequently extracted from the resin by dichloromethane/trifluoroacetic acid (TFA) 3:1 (v/v) followed by rotary evaporation. The crude peptide extract was redissolved at a concentration of 100 mg/ml in chloroform/methanol 1:1 (v/v) containing 5% $H_2O$. An aliquot of 10 mg was applied on a Sephadex LH-60 column (40×1 cm) in the same solvent (Curstedt, T. et al. (1987) Eur. J. Biochem. 168, 255–262). Fractions of 2.5 ml were collected and absorbencies at 214 and 280 nm were measured. Identification and quantitation were performed by amino acid analysis.

For acylation, the purified peptide (typically about 5 mg) is dried, dissolved in distilled TFA (100 μl) and acyl chloride (10–20 equivalents compared to peptide) is added. After 10 minutes the reaction is quenched with 80% aqueous ethanol (1.9 ml). Purification of acyl peptides is performed using chromatography over Lipidex 5000 in ethylene chloride/methanol 1:4 (v/v) followed by reversed-phase HPLC over a C18 column using a linear gradient of 2-propanol/0.1% TFA running into 60% (aqueous) methanol/0.1% TFA or 75% (aqueous) ethanol/0.1% TFA.

EXAMPLE 2

Biochemical Characterisation

The purity of the peptide was checked by sodium-dodecylsulphate (SDS) polyacrylamide gel electrophoresis (PAGE) (Phast-system, Pharmacia, Sweden) and by reversed phase high performance liquid chromatography (HPLC), using a $C_{18}$ column and a linear gradient of 60% aqueous methanol/0.1% TFA and isopropanol/0.1% TFA (Gustafsson, M. et al. (1997) Biochem. J. 326, 799–806).

Molecular masses were determined by matrix-assisted laser desorption ionisation-time-of-flight (MALDI-TOF) mass spectrometry (Lasermat 2000, Finnigan MAT) calibrated with vasoactive intestinal peptide ($M_r$ 3326.8).

Peptide secondary structure was investigated using circular dichroism (CD) spectroscopy (Jasco-720 Jasco, Japan). After solubilisation with triflouroethanol (TFE) spectra were recorded from 260 to 184 nm with a scan speed of 20 nm/min and a resolution of 2 data points/nm. The residual molar ellipticy was calculated and expressed in $kdeg \times cm^2/dmol$. Molar ellipticities at 208 and 222 nm were utilised for estimating the content of helical structure (Barrow, C. J. et al. (1992) J. Mol. Biol. 225, 1075–1093).

Secondary structure investigations of SP-C(LKS) using CD spectroscopy showed a spectrum typical for α-helical peptides and an α-helical content of approximately 75% was estimated from the 208 nm and 222 nm minima. The secondary structure remained stable following stepwise dilution with $H_2O$ until 12% TFE provided that the peptide was solubilized in neat TFE.

SDS-PAGE of SP-C(LKS) showed a single band similar to native SP-C while SP-C(Leu) which lacks Lys in the helical part forms oligomers. In contrast to our experience with SP-C(Leu)/lipid mixtures, which are difficult to solubilize in higher concentrations than 20 mg/ml (Nilsson, G. et al. (1998) Eur. J. Biochem. 255, 116–124.), it was possible to make a SP-C(LKS)/lipid mixture with a lipid concentration of 80 mg/ml and a polypeptide/lipid ratio of 0.03.

EXAMPLE 3

Preparation of Peptide/Lipid Mixtures

DPPC, PG and PA were all purchased from Sigma Chemical Co. (St Louis, Mo.). The lipids, dissolved in chloroform/methanol 98:2 (v/v), were mixed in the proportions DPPC:PG:PA 68:22:9 (w/w/w) or DPPC/PG 7:3 (w/w). Surfactant preparations were prepared by adding SP-C(LKS) alone or SP-C(LKS) and SP-B, to each of the lipid mixtures, at total polypeptide/lipid weight ratios of 0–0.05. The mixtures were evaporated under nitrogen and resuspended in 150 mmol/l NaCl or in 10 mmol/l Hepes buffer pH 6,9 containing 140 mmol/l NaCl and 2.0 mmol/l CaCl$_2$, at lipid concentrations of 10–80 mg/ml. Repeated freezing and sonication (50 W, 48 kHz) were performed until homogeneous suspensions were achieved. In some cases the final suspensions were incubated at 45° C. for 1 h.

Surfactant preparations suspended in 150 mmol/l NaCl have a pH of 3.5–5.5. The lower pH-values 3.5–4.5 were observed in preparations containing SP-B. Since native SP-B is purified using acidified organic solvents (Curstedt, T. et al. (1987) Eur. J. Biochem. 168, 255–262) small amounts of acid may remain in the preparations. Near physiological pH was obtained by suspending the surfactant preparation in Hepes buffer pH 6.9, containing 140 mmol/l NaCl and 2 mmol/l CaCl$_2$ (Table 1). Compared to the corresponding preparations in unbuffered saline there were no changes of $\gamma_{max}$ or $\gamma_{min}$ when DPPC/PG 7:3 (w/w) was used as the lipid mixture. However when PA was included in the lipid mixture both $\gamma_{max}$ and $\gamma_{min}$ increased at the higher pH (Tables 1 and 2).

TABLE 1

Surface properties of preparations of artificial surfactant in physiological saline solution
Measurements were carried out directly after the preparation of the samples or after incubation for 1 hour at 45° C. The phospholipids conc. was 10 mg/ml in NaCl 150 mmol/l. The recordings were obtained at different periods of time with a pulsating bubble surfactometer at 37° C., 50% surface compression and at a rate of 40 cycles per min. The values are the mean (standard deviation) of 3–5 measurements. Abbreviations are defined in the text.

| Surfactant preparation | | | | Surface tension (mN/m) | | | | | |
|---|---|---|---|---|---|---|---|---|---|
| SP-C (LKS) | SP-B | | Incubation | 7,5 s | | 1 min | | 5 min | |
| (% w/w) | (% w/w) | Phospholipids | temperature | $\gamma_{min}$ | $\gamma_{max}$ | $\gamma_{min}$ | $\gamma_{max}$ | $\gamma_{min}$ | $\gamma_{max}$ |
| 3 | — | DPPC/PG/PA | — | <1 | 41(1) | <1 | 41(1) | <1 | 41(0) |
| 3 | — | DPPC/PG/PA | 45° C. | <1 | 41(1) | <1 | 41(1) | <1 | 41(1) |
| 3 | 2 | DPPC/PG/PA | — | <1 | 33(2) | <1 | 33(2) | <1 | 33(2) |
| 3 | 2 | DPPC/PG/PA | 45° C. | <1 | 34(1) | <1 | 34(2) | <1 | 25(2) |
| 3 | — | DPPC/PG | — | 12 | 39(5) | 14(4) | 42(4) | 9(5) | 42(2) |
| 3 | — | DPPC/PG | 45° C. | 8(3) | 35(5) | 9(3) | 39(5) | 6(4) | 42(3) |
| 3 | 2 | DPPC/PG | — | 2(1) | 31(1) | 2(1) | 31(3) | 2(1) | 33(1) |
| 3 | 2 | DPPC/PG | 45° C. | 3(3) | 29(3) | 1(1) | 33(2) | 1(0) | 36(1) |
| 3 | 1 | DPPC/PG | — | <1 | 24(4) | 1(2) | 26(4) | <1 | 31(1) |
| 3 | 0.5 | DPPC/PG | 45° C. | 4(2) | 29(1) | 4(3) | 29(2) | 3(1) | 34(2) |

TABLE 2

Surface properties of preparations of artificial surfactant in buffered salt solution
Measurements were carried out on samples containing phospholipids at the conc. of 10 mg/ml in Hepes buffer (pH 6.9), in turn containing NaCl 140 mmol/l and CaCl$_2$ 2.0 mmol/l. The recordings were obtained at different periods of time with a pulsating bubble surfactometer at 37° C., 50% surface compression and at a rate of 40 cycles per min. The values are the mean (standard deviation) of 3–5 measurements. Abbreviations are defined in the text.

| Surfactant preparation | | | Surface tension (mN/m) | | | | | |
|---|---|---|---|---|---|---|---|---|
| SP-C (LKS) | SP-B | | 7.5 s | | 1 min | | 5 min | |
| (% w/w) | (% w/w) | Phospholipids | $\gamma_{min}$ | $\gamma_{max}$ | $\gamma_{min}$ | $\gamma_{max}$ | $\gamma_{min}$ | $\gamma_{max}$ |
| 3 | — | DPPC/PG/PA | 4 (1) | 44 (2) | 5 (2) | 47 (2) | 7 (2) | 50 (1) |
| 3 | 2 | DPPC/PG/PA | 3 (3) | 38 (3) | 4 (4) | 40 (2) | 3 (3) | 44 (2) |
| 3 | — | DPPC/PG | 15 (3) | | 16 (2) | 42 (3) | 13 (3) | 44 (3) |
| 3 | 2 | DPPC/PG | 39 (4) | | 1 (1) | 29 (3) | <1 | 35 (1) |
| | | | 2 (2) | 26 (3) | | | | |

EXAMPLE 4

Preparation of Phospholipid Mixtures with SP-C(LKS) and Polymyxin B

DPPC and PG were purchased from Sigma Chemical Co (St Louis, Mo.). The phospholipids, dissolved in chloroform/methanol 98:2 (v/v), were mixed in the proportions DPPC/PG 7:3 (w/w). SP-C (LKS) was added to the phospholipid mixtures, at a total polypeptide/phospholipid weight ratio of 0.03. The mixtures were evaporated under nitrogen and resuspended at room temperature in 10 mmol/l Hepes buffer pH 6,9 containing 140 mmol/l NaCl and 2.0 mmol/l $CaCl_2$ or in the same buffer containing 0.01% polymyxin B (PxB) (Sigma Chemical Co, St Louis, Mo.). Repeated freezing and sonication (50 W, 48 kHz) were performed until homogeneous suspensions were achieved. The final phospholipid concentration for both preparations was 10 mg/ml. Addition of PxB decreased both $\gamma_{min}$ and $\gamma_{max}$ and optimal surface activity was obtained (Table 3).

bubble surface and at a frequency of 40 cycles per min. All measurements were performed for 5 min and at a lipid concentration of 10 mg/ml. The pressure gradiens across the bubble wall were measured at specific time intervals were measured and used to calculate surface tensions at minimum ($\gamma_{min}$) and maximum ($\gamma_{max}$) bubble size.

In the pulsating bubble surfactometer 3 weight % SP-C (LKS) in DPPC:PG:PA, 68:22:9 (w/w/w,) produced a surface tension of less than 1 mN/m at minimum bubble radius ($\gamma_{min}$) while a $\gamma_{min}$ of 9–14 mN/m was observed with 3 weight % SP-C(LKS) in DPPC:PG, 7:3 (w/w) (Table 1). The surface tension at maximum bubble radius ($\gamma_{max}$) was about 40 mN/m in both cases. Addition of 2 weight % SP-B gave $\gamma_{max}$-values of 31–33 mN/m and $\gamma_{min}$ of 0–2 mN/m for both lipid preparations. These values are very similar to those obtained with surfactant preparations isolated from natural sources (Robertson, B. et al. (1990) Prog. Respir. Res. 25, 237–246). Incubation of the preparations at 45° C. for 1 h had no significant effect on surface activity (Table 1). Decreasing the amount of SP-B to 0.5 weight % in 3 weight

TABLE 3

Surface properties of artificial surfactant with and without polymyxin B
The recordings were obtained at different periods of time with a pulsating bubble surfactometer at 37° C. and 50% surface compression at a rate of 40 cycles per min. The values are the mean (SD) of 5–11 measurements. Abbreviations are defined in the text.

| Surfactant preparation | | | Surface tension (mN/m) | | | | | |
|---|---|---|---|---|---|---|---|---|
| | | | 7.5 s | | 1 min | | 5 min | |
| SP-C (LKS) (% w/w) | PxB (% w/w) | Phospholipids | $\gamma_{min}$ | $\gamma_{max}$ | $\gamma_{min}$ | $\gamma_{max}$ | $\gamma_{min}$ | $\gamma_{max}$ |
| 3 | — | DPPC/PG | 15 (3) | 39 (4) | 16 (2) | 42 (3) | 13 (3) | 44 (3) |
| 3 | 1 | DPPC/PG | 3 (2) | 29 (3) | 2 (2) | 31 (4) | 1 (1) | 34 (2) |

EXAMPLE 5

Biophysical Characterisation

Surface spreading kinetics were measured at about 34–37° C. with a Wilhelmy surface balance (Biegler, Vienna, Austria). Surface tension was monitored for 10 min using a platinium plate connected to a strain gauge and inserted 1 mm in to a hypophase of 20 ml of 150 mmol/l NaCl in a teflon trough. The suspensions were added as droplets, totally 1 mg of lipids, onto the hypophase, 4 cm from the platinium plate.

Kinetic measurements of 3 weight % SP-C(LKS) in DPPC/PG, 7:3 (w/w), using the Wilhelmy balance showed a rapid spreading with a surface tension of 28 mN/m after 3 s (FIG. 2). The spreading was somewhat slower using 1 weight % SP-C(LKS) in the same lipid mixture (data not shown). Addition of 2 weight % SP-B did not significantly change spreading velocity or equilibrium surface tension (FIG. 2). No improvements were observed after incubation of the mixture for 1 h at 45° C. (data not shown). Similar results were obtained with DPPC:PG:PA, 68:22:9 (w/w/w) as the lipid mixture (data not shown).

Dynamic surface tension was recorded using a pulsating bubble surfactometer (Surfactometer International, Toronto, Canada) at 37° C. during 50% cyclic compression of the % SP-C(LKS) in DPPC:PG 7:3 (w/w) tended to increase $\gamma_{min}$ although the results did not reach statistical significance (Table 1). In contrast to SP-B, addition of 2 weight % $KL_4$ (Cochrane, C. G. and Revak, S. D. (1991) Science 254, 566–568) to 3 weight % SP-C(LKS) in DPPC:PG:PA 68:22:9 (w/w) did not reduce $\gamma_{max}$ which remained relatively high at 41–42 mN/m.

EXAMPLE 6

Comparison Between Mixtures Containing Dipalmitoylated and Non-Palmitoylated Reference Peptides Surfactant preparations were prepared by adding 3% w/w SP-C(Leu) or dipalmitoylated SP-C(Leu) to each lipid mixtures, made of DPPC/PG/PA 68:22:9 w/w/w. The mixtures were evaporated under nitrogen and resuspended in 150 mmol/l NaCl at lipid concentrations of 10 mg/ml. In the samples in which a SP-B substituent was also used, 1% w/w of polymyxin B was added.

Mixtures containing dipalmitoylated SP-C(Leu), with or without polymyxin B, exhibit significant improvement especially in reducing $\gamma_{max}$ at 5 min and $\gamma_{min}$ at earlier time intervals.

TABLE 4

Surface properties
Surface tension of the mixtures was obtained with a pulsating bubble surfactometer. After two minutes of equilibration, the recordings were obtained at different periods, at 37° C., 50% surface compression and at a rate of 40 cycles per min.

| Surfactant preparation | | | | | | | | |
|---|---|---|---|---|---|---|---|---|
| SP-C (Leu) (weight %) | Dipalm. SP-C (Leu) (weight %) | PxB (weight %) | \multicolumn{6}{c}{Surface tension (mN/m)} |
| | | | 7,5 s | | 1 min | | 5 min | |
| | | | $\gamma_{min}$ | $\gamma_{max}$ | $\gamma_{min}$ | $\gamma_{max}$ | $\gamma_{min}$ | $\gamma_{max}$ |
| 1 | | | 11 | 39 | 6,2 | 39 | 2 | 42 |
| 1 | | 1 | 3 | 37 | 3 | 38 | 0 | 40 |
| | 1 | — | 1 | 34 | 1 | 35 | 1 | 36 |
| | 1 | 1 | 0 | 29 | 0 | 34 | 0 | 35 |

EXAMPLE 7

In Vivo Determination

The effect of surfactant therapy on the mechanical properties of immature lungs was evaluated in 9 preterm newborn rabbits with a gestational age of 27 days. The animals were tracheotomized at birth and five of them received, via the tracheal cannula, twice 2.5 ml/kg of artificial surfactant containing DPPC, PG, and SP-C (LKS), with or without polymyxin B, in the proportions given above. Total phospholipid concentration of the exogenous surfactant material was 40 mg/ml. Two animals serving as negative control received no material via the tracheal tube, and another two serving as positive control were treated with the same dose of modified natural surfactant (Curosurf, Chiesi Farmaceutici Spa, Parma, Italy), diluted to 40 mg/ml. One animal was treated with a mixture of DPPC and PG in saline (same concentrations as above) at a dose of 2.5 ml/kg. All animals were kept in body plethysmograph boxes at a temperature of 37° C. and ventilated in parallel for 60 min with 100% oxygen, using a Servo Ventilator 900B (Siemens-Elema, Solna, Sweden) set at a frequency of 40 min and 50% inspiration time. Tidal volumes were measured with a pneumotachygraph connected to each plethysmograph box. The animals were ventilated with a standardized tidal volume of 8–10 ml/kg and without a positive end-expiratory pressure (PEEP). Lung-thorax compliance was defined as the ratio between tidal volume and peak inspiratory pressure, and expressed as ml/cm $H_2O$ kg.

In comparison with the non-treated control animal, compliance was improved significantly in animals treated with the artificial surfactant, especially in the animal receiving surfactant containing polymyxin B. Notably, the improvement appears to be superior to that seen after treatment with a similar dose of modified natural surfactant (FIG. 3).

The sequence of human SP-C (SEQ ID NO: 13) is taken from Johansson, J., et al. (1988) FEBS Lett. 232, 61–64 and that of SP-C(Leu) (SEQ ID NO: 14) from Nilsson, G., et al. (1999) Eur. J. Biochem, 255, 116–124). SP-C(LKS) (SEQ ID NO: 7) is based on the primary structure of SP-C but all Val residues at the positions 16–28 with the exception of position 17 are replaced with Leu residues, Lys residues have been introduced at positions 17, 22, and 27, and the palmitoylated Cys at positions 5 and 6 are replaced with Ser.

Figure 1:
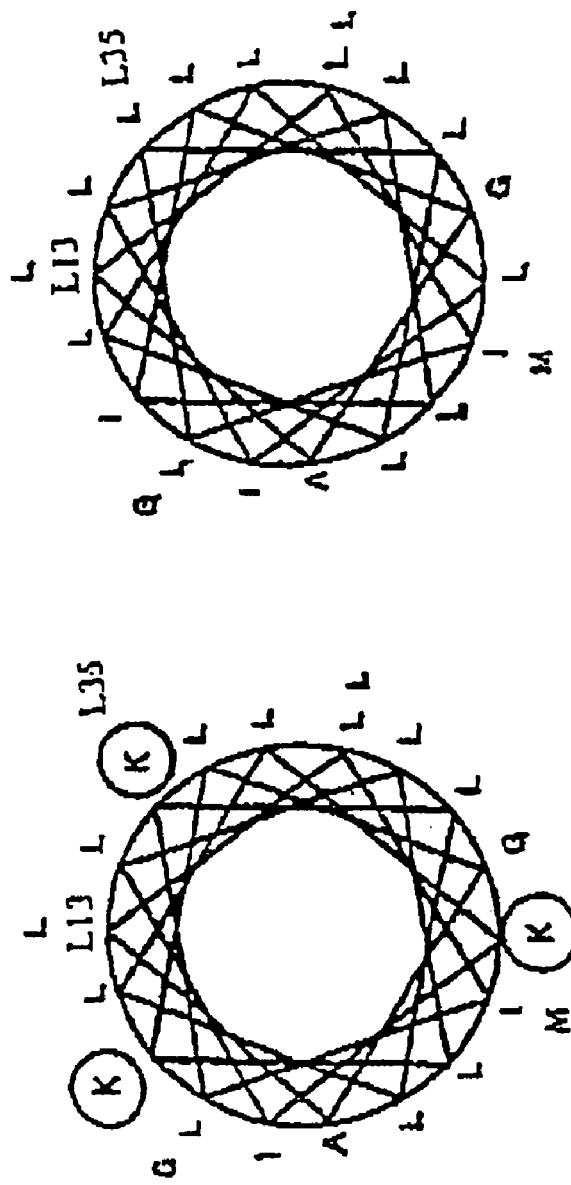
FIG. 1. Amino acid sequences and helical wheel presentations of SP-C and its analogues.
Figure 2:
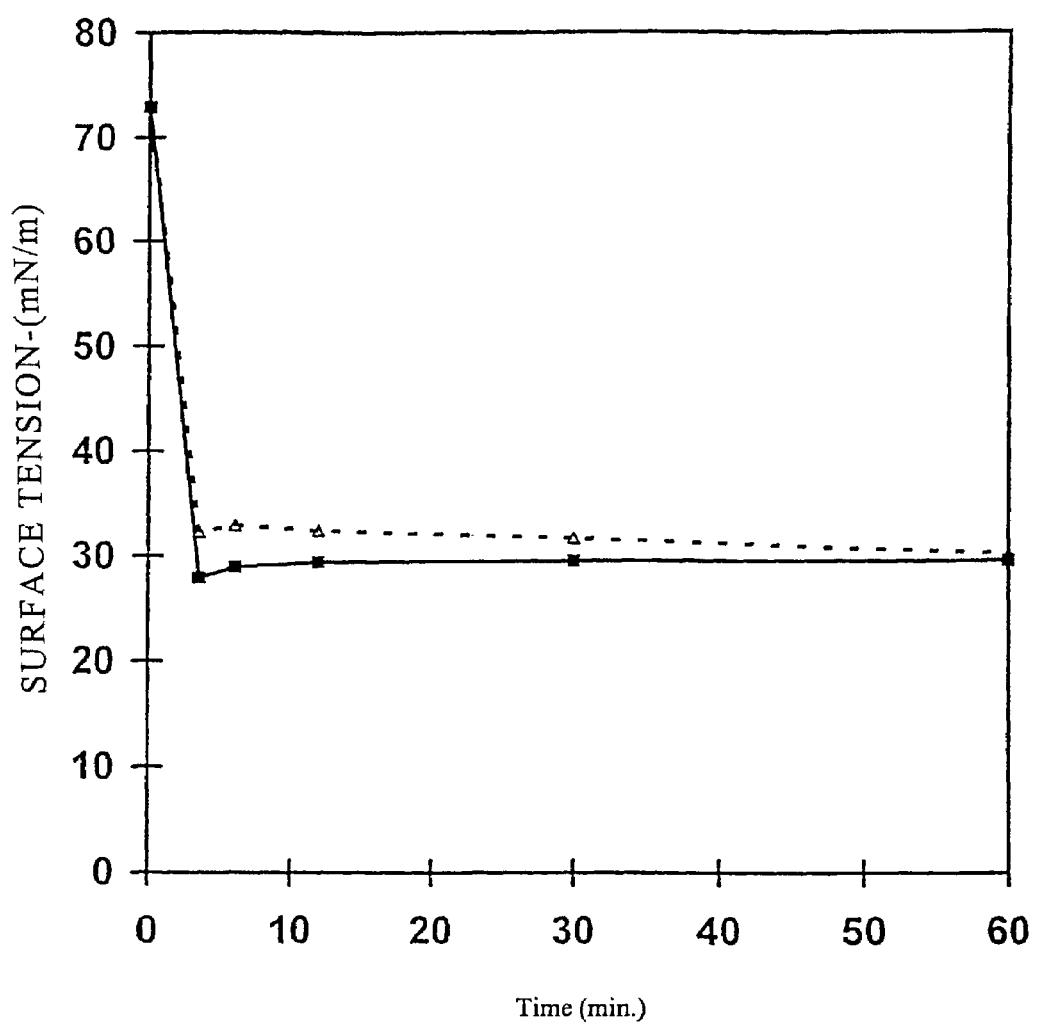

FIG. 2. Surface spreading of synthetic surfactant preparations.

Spreading kinetics of 3 weight % SP-C(LKS) (filled squares, solid line) and of 3 weight % SP-C(LKS) with addition of 2 weight % SP-B (open triangles, dotted line). All preparations were examined at a concentration of 10 mg/ml of DPPC/PG, 7:3 (w/w) in 150 mmol/l NaCl. The recordings were obtained with a Wilhelmy balance and each datapoint is the mean of three different recordings.

Figure 3:
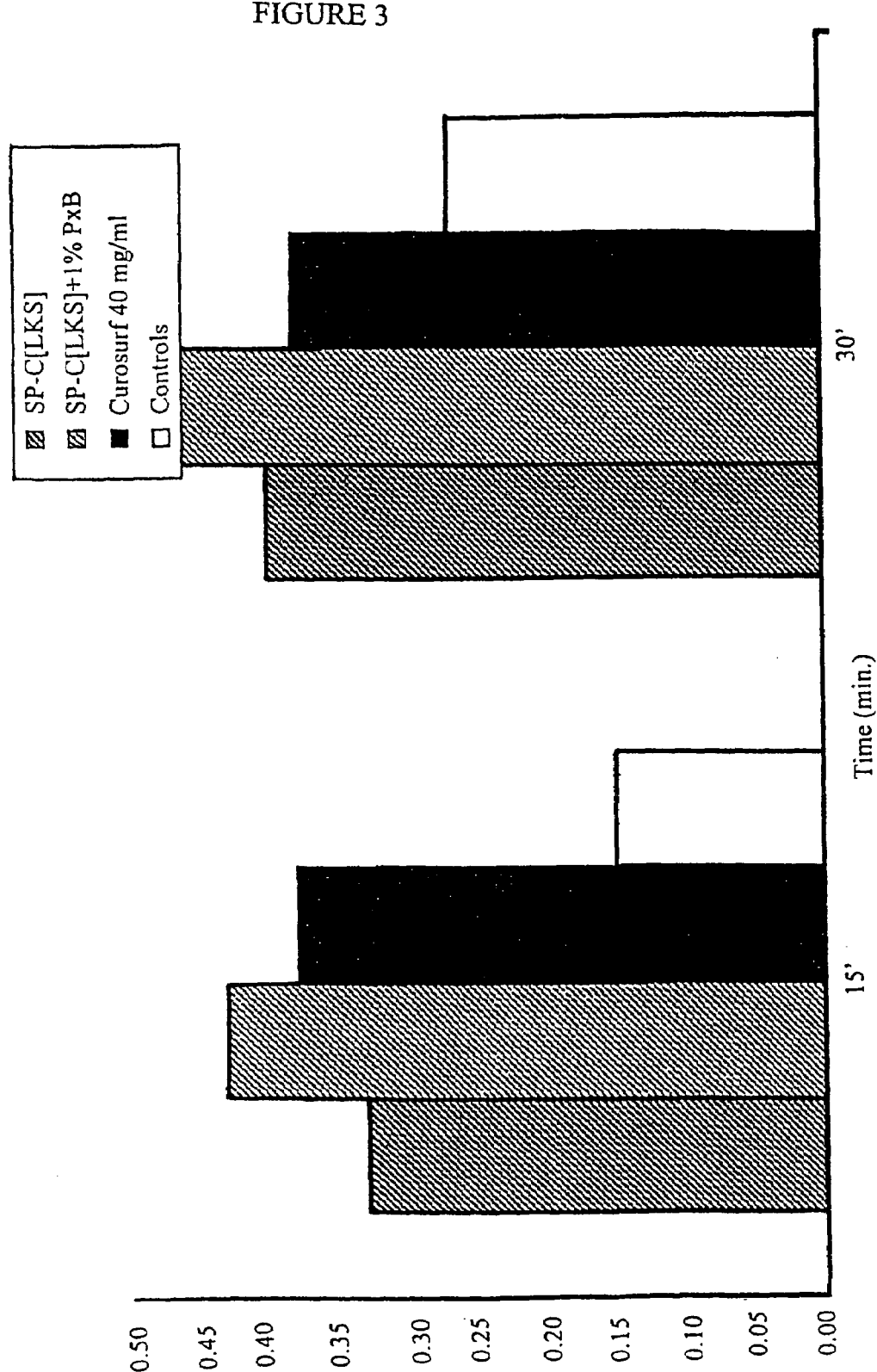

FIG. 3 In vivo results

Lung-thorax compliance in 5 premature newborn rabbits (gestational age of 27 days) ventilated with a standardized tidal volume of 8–10 ml/kg and without a positive end-expiratory pressure (PEEP). Compliance is improved significantly in treated animals. Addition of polymyxin B (PxB) appears to increase the effect of the artificial surfactant. The concentration of phospholipids is the same in all surfactant preparations, i.e. 40 mg/ml.

The invention claimed is:

1. An SP-C analog having the following general formula $F_eG_fIPSSPVHLKR(X_aB)_n(X_bB)_nX_cBX_d GALLMGL$ wherein:
   X is an amino acid selected from the group consisting of I, L, and Nle (norleucine);
   B is an amino acid selected from the group consisting of K, W, F, Y, and Ornithine;
   a is an integer from 1 to 19;
   b is an integer from 1 to 19;
   c is an integer from 1 to 21;
   d is an integer from 0 to 20;
   e=f=0 or 1;
   n is 0 or 1; and
   wherein:
   $(X_aB)_n(X_bB)_nX_cBX_d$ is a sequence having a maximum of 22 amino acids.

2. An SP-C analog according to claim 1, having formula (Ia):
   $FGIPSSPVHLKRX_4BX_4BX_4BXGALLMGL$ (SEQ ID NO: 2).

3. An SP-C analog according to claim 1, having formula (Ib):
FGIPSSPVHLKRX$_5$BX$_5$BX$_4$GALLMGL (SEQ ID NO: 3).

4. An SP-C analog according to claim 1, having formula (Ic):
FGIPSSPVHLKRX$_4$BX$_{11}$GALLMGL (SEQ ID NO: 4).

5. An SP-C analog according to claim 1, having formula (Id):
FGIPSSPVHLKRX$_8$BX$_7$GALLMGL (SEQ ID NO: 5).

6. An SP-C analog according to claim 1, having formula (Ie):
FGIPSSPVHLKRX$_{11}$BX$_4$GALLMGL (SEQ ID NO: 6).

7. An SP-C analog according to claim 1, in which the Ser residues are acylated.

8. An SP-C analog according to claim 1, in which B is Lysine or Phenylalanine.

9. An SP-C analog according to claim 8, selected from the group consisting of:
SP-C (LKS) FGIPSSPVHLKRLLILKLLLLKILLLKL-GALLMGL (SEQ ID NO: 7);
SP-C (LKS)$_1$ FGIPSSPVHLKRLLILLKLLLLIKLLIL-GALLMGL (SEQ ID NO: 8);
SP-C (LKS)$_2$ FGIPSSPVHLKRLLILKLLLLLILLLIL-GALLMGL (SEQ ID NO: 9);
SP-C (LKS)$_3$ FGIPSSPVHLKRLLILLLLLKLILLLIL-GALLMGL (SEQ ID NO: 10);
SP-C (LKS)$_4$ FGIPSSPVHLKRLLILLLLLLLIKLLIL-GALLMGL (SEQ ID NO: 11); and
SP-C (LFS) FGIPSSPVHLKRLLILFLLLLFILLLFL-GALLMGL (SEQ ID NO: 12).

10. A synthetic surfactant comprising at least one SP-C analog of claim 1 in admixture with at least one lipid and/or phospholipid.

11. A synthetic surfactant according to claim 10, in which said lipids and/or phospholipids comprise DPPG, PG, and/or PA.

12. A synthetic surfactant according to claim 10, further comprising SP-B or an active derivative thereof, or a polymyxin.

13. A synthetic surfactant according to claim 10, in the form of a solution, dispersion, suspension, or a dry powder.

14. The SP-C analogue of claim 1 wherein the (X$_a$B)$_n$ (X$_b$B)$_n$X$_c$BX$_d$ sequence has from 10 to 22 amino acids.

15. The SP-C analogue of claim 7, wherein the Ser residues are acylated with palmitoyl groups.

16. A pharmaceutically active synthetic surfactant comprising the SP-C analog of claim 1.

17. A method of treating a surfactant deficiency comprising administering an effective amount of the SP-C analog of claim 1 to a subject in need thereof.

18. A pharmaceutically active synthetic surfactant comprising the surfactant of claim 10, wherein said surfactant comprises polymyxin.

19. A pharmaceutically active synthetic surfactant comprising the surfactant of claim 10, wherein said surfactant comprises polymyxin B.

20. A method of treating surfactant deficiencies or dysfunction, or serious otitis media, comprising administering an effective amount of the surfactant of claim 10 to a subject in need thereof, wherein said surfactant comprises polymyxin.

21. A method of treating a surfactant deficiency or dysfunction, or serious otitis media, comprising administering to a subject in need thereof an effective amount of the surfactant of claim 10 wherein said surfactant comprises polymyxin B.

22. The method of claim 17, wherein said subject has respiratory distress syndrome.

23. The method of claim 20, wherein said subject has respiratory distress syndrome.

24. The method of claim 21, wherein said subject has respiratory distress syndrome.

25. The SP-C analog of claim 1, wherein B is selected from the group consisting of K and F.

26. The SP-C analog of claim 1, wherein X is selected from the group consisting of I and L.

27. The SP-C analog of claim 1, wherein B is selected from the group consisting of K and F; and X is selected from the group consisting of I and L.

28. A pharmaceutically active synthetic surfactant comprising the surfactant of claim 10, wherein said surfactant of claim 10 contains at least one phospholipid selected from the group consisting of DPPC and PG.

29. A method of treating a surfactant deficiency or dysfunction or serious otitis media, comprising:
administering to a subject in need thereof an effective amount of the surfactant of claim 10, wherein said surfactant of claim 10 contains at least one phospholipid selected from the group consisting of DPPC and PG.

30. The SP-C analog of claim 1, which does not give rise to self-oligomerization.

31. The SP-C analog of claim 1, which folds like the native peptide and interacts with surfactant lipids.

* * * * *

UNITED STATES PATENT AND TRADEMARK OFFICE
CERTIFICATE OF CORRECTION

| | | |
|---|---|---|
| PATENT NO. | : 7,053,044 B1 | Page 1 of 1 |
| APPLICATION NO. | : 09/926009 | |
| DATED | : May 30, 2006 | |
| INVENTOR(S) | : Curstedt et al. | |

It is certified that error appears in the above-identified patent and that said Letters Patent is hereby corrected as shown below:

On the title page, Item (75), the 4th inventor has been omitted. Item (75) should read:

-- (75) Inventors: Tore Curstedt, Parma (IT); Jan Johansson, Parma (IT); Hans Jörnvall, Parma (IT); Bengt Robertson, Parma (IT); Paolo Ventura, Parma (IT) --

Signed and Sealed this

Twenty-first Day of November, 2006

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 101
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (1)..(1)
<223> OTHER INFORMATION: X = Phe and may or may not be present
<221> NAME/KEY: MISC_FEATURE
<222> LOCATION: (2)..(2)
<223> OTHER INFORMATION: X = Gly and may or may not be present
<221> NAME/KEY: MISC_FEATURE
<222> LOCATION: (5)..(5)
<223> OTHER INFORMATION: X = Ser, Cys, Phe where Ser and Cys are
      optionally linked bia ester or thio-ester bonds with acyl groups
      containing 12 to 22 carbons atoms linked
<221> NAME/KEY: MISC_FEATURE
```

-continued

```
<222> LOCATION: (6)..(6)
<223> OTHER INFORMATION: X = Ser, Cys, Phe where Ser and Cys are
      optionally linked bia ester or thio-ester bonds with acyl groups
      containing 12 to 22 carbons atoms linked
<221> NAME/KEY: MISC_FEATURE
<222> LOCATION: (13)..(13)
<223> OTHER INFORMATION: X = Val, Leu, Ile or Nle and may or may not be
      present
<221> NAME/KEY: MISC_FEATURE
<222> LOCATION: (14)..(14)
<223> OTHER INFORMATION: X = Val, Leu, Ile or Nle and may or may not be
      present
<221> NAME/KEY: MISC_FEATURE
<222> LOCATION: (15)..(15)
<223> OTHER INFORMATION: X = Val, Leu, Ile or Nle and may or may not be
      present
<221> NAME/KEY: MISC_FEATURE
<222> LOCATION: (16)..(16)
<223> OTHER INFORMATION: X = Val, Leu, Ile or Nle and may or may not be
      present
<221> NAME/KEY: MISC_FEATURE
<222> LOCATION: (17)..(17)
<223> OTHER INFORMATION: X = Val, Leu, Ile or Nle and may or may not be
      present
<221> NAME/KEY: MISC_FEATURE
<222> LOCATION: (18)..(18)
<223> OTHER INFORMATION: X = Val, Leu, Ile or Nle and may or may not be
      present
<221> NAME/KEY: MISC_FEATURE
<222> LOCATION: (19)..(19)
<223> OTHER INFORMATION: X = Val, Leu, Ile or Nle and may or may not be
      present
<221> NAME/KEY: MISC_FEATURE
<222> LOCATION: (20)..(20)
<223> OTHER INFORMATION: X = Val, Leu, Ile or Nle and may or may not be
      present
<221> NAME/KEY: MISC_FEATURE
<222> LOCATION: (21)..(21)
<223> OTHER INFORMATION: X = Val, Leu, Ile or Nle and may or may not be
      present
<221> NAME/KEY: MISC_FEATURE
<222> LOCATION: (22)..(22)
<223> OTHER INFORMATION: X = Val, Leu, Ile or Nle and may or may not be
      present
<221> NAME/KEY: MISC_FEATURE
<222> LOCATION: (23)..(23)
<223> OTHER INFORMATION: X = Val, Leu, Ile or Nle and may or may not be
      present
<221> NAME/KEY: MISC_FEATURE
<222> LOCATION: (24)..(24)
<223> OTHER INFORMATION: X = Val, Leu, Ile or Nle and may or may not be
      present
<221> NAME/KEY: MISC_FEATURE
<222> LOCATION: (25)..(25)
<223> OTHER INFORMATION: X = Val, Leu, Ile or Nle and may or may not be
      present
<221> NAME/KEY: MISC_FEATURE
<222> LOCATION: (26)..(26)
<223> OTHER INFORMATION: X = Val, Leu, Ile or Nle and may or may not be
      present
<221> NAME/KEY: MISC_FEATURE
<222> LOCATION: (27)..(27)
<223> OTHER INFORMATION: X = Val, Leu, Ile or Nle and may or may not be
      present
<221> NAME/KEY: MISC_FEATURE
<222> LOCATION: (28)..(28)
<223> OTHER INFORMATION: X = Val, Leu, Ile or Nle and may or may not be
      present
<221> NAME/KEY: MISC_FEATURE
<222> LOCATION: (29)..(29)
<223> OTHER INFORMATION: X = Val, Leu, Ile or Nle and may or may not be
      present
<221> NAME/KEY: MISC_FEATURE
<222> LOCATION: (30)..(30)
<223> OTHER INFORMATION: X = Val, Leu, Ile or Nle and may or may not be
      present
<221> NAME/KEY: MISC_FEATURE
<222> LOCATION: (31)..(31)
<223> OTHER INFORMATION: X = Val, Leu, Ile or Nle and may or may not be
```

-continued

```
       present
<221> NAME/KEY: MISC_FEATURE
<222> LOCATION: (32)..(32)
<223> OTHER INFORMATION: X = Val, Leu, Ile or Nle and may or may not be
       present
<221> NAME/KEY: MISC_FEATURE
<222> LOCATION: (34)..(34)
<223> OTHER INFORMATION: X = Val, Leu, Ile or Nle and may or may not be
       present
<221> NAME/KEY: MISC_FEATURE
<222> LOCATION: (35)..(35)
<223> OTHER INFORMATION: X = Val, Leu, Ile or Nle and may or may not be
       present
<221> NAME/KEY: MISC_FEATURE
<222> LOCATION: (36)..(36)
<223> OTHER INFORMATION: X = Val, Leu, Ile or Nle and may or may not be
       present
<221> NAME/KEY: MISC_FEATURE
<222> LOCATION: (37)..(37)
<223> OTHER INFORMATION: X = Val, Leu, Ile or Nle and may or may not be
       present
<221> NAME/KEY: MISC_FEATURE
<222> LOCATION: (38)..(38)
<223> OTHER INFORMATION: X = Val, Leu, Ile or Nle and may or may not be
       present
<221> NAME/KEY: MISC_FEATURE
<222> LOCATION: (39)..(39)
<223> OTHER INFORMATION: X = Val, Leu, Ile or Nle and may or may not be
       present
<221> NAME/KEY: MISC_FEATURE
<222> LOCATION: (40)..(40)
<223> OTHER INFORMATION: X = Val, Leu, Ile or Nle and may or may not be
       present
<221> NAME/KEY: MISC_FEATURE
<222> LOCATION: (41)..(41)
<223> OTHER INFORMATION: X = Val, Leu, Ile or Nle and may or may not be
       present
<221> NAME/KEY: MISC_FEATURE
<222> LOCATION: (42)..(42)
<223> OTHER INFORMATION: X = Val, Leu, Ile or Nle and may or may not be
       present
<221> NAME/KEY: MISC_FEATURE
<222> LOCATION: (43)..(43)
<223> OTHER INFORMATION: X = Val, Leu, Ile or Nle and may or may not be
       present
<221> NAME/KEY: MISC_FEATURE
<222> LOCATION: (44)..(44)
<223> OTHER INFORMATION: X = Val, Leu, Ile or Nle and may or may not be
       present
<221> NAME/KEY: MISC_FEATURE
<222> LOCATION: (45)..(45)
<223> OTHER INFORMATION: X = Val, Leu, Ile or Nle and may or may not be
       present
<221> NAME/KEY: MISC_FEATURE
<222> LOCATION: (46)..(46)
<223> OTHER INFORMATION: X = Val, Leu, Ile or Nle and may or may not be
       present
<221> NAME/KEY: MISC_FEATURE
<222> LOCATION: (47)..(47)
<223> OTHER INFORMATION: X = Val, Leu, Ile or Nle and may or may not be
       present
<221> NAME/KEY: MISC_FEATURE
<222> LOCATION: (48)..(48)
<223> OTHER INFORMATION: X = Val, Leu, Ile or Nle and may or may not be
       present
<221> NAME/KEY: MISC_FEATURE
<222> LOCATION: (49)..(49)
<223> OTHER INFORMATION: X = Val, Leu, Ile or Nle and may or may not be
       present
<221> NAME/KEY: MISC_FEATURE
<222> LOCATION: (50)..(50)
<223> OTHER INFORMATION: X = Val, Leu, Ile or Nle and may or may not be
       present
<221> NAME/KEY: MISC_FEATURE
<222> LOCATION: (51)..(51)
<223> OTHER INFORMATION: X = Val, Leu, Ile or Nle and may or may not be
       present
<221> NAME/KEY: MISC_FEATURE
<222> LOCATION: (52)..(52)
```

-continued

```
<223> OTHER INFORMATION: X = Val, Leu, Ile or Nle and may or may not be
      present
<221> NAME/KEY: MISC_FEATURE
<222> LOCATION: (54)..(54)
<223> OTHER INFORMATION: X = Val, Leu, Ile or Nle and may or may not be
      present
<221> NAME/KEY: MISC_FEATURE
<222> LOCATION: (55)..(55)
<223> OTHER INFORMATION: X = Val, Leu, Ile or Nle and may or may not be
      present
<221> NAME/KEY: MISC_FEATURE
<222> LOCATION: (56)..(56)
<223> OTHER INFORMATION: X = Val, Leu, Ile or Nle and may or may not be
      present
<221> NAME/KEY: MISC_FEATURE
<222> LOCATION: (57)..(57)
<223> OTHER INFORMATION: X = Val, Leu, Ile or Nle and may or may not be
      present
<221> NAME/KEY: MISC_FEATURE
<222> LOCATION: (58)..(58)
<223> OTHER INFORMATION: X = Val, Leu, Ile or Nle and may or may not be
      present
<221> NAME/KEY: MISC_FEATURE
<222> LOCATION: (59)..(59)
<223> OTHER INFORMATION: X = Val, Leu, Ile or Nle and may or may not be
      present
<221> NAME/KEY: MISC_FEATURE
<222> LOCATION: (60)..(60)
<223> OTHER INFORMATION: X = Val, Leu, Ile or Nle and may or may not be
      present
<221> NAME/KEY: MISC_FEATURE
<222> LOCATION: (61)..(61)
<223> OTHER INFORMATION: X = Val, Leu, Ile or Nle and may or may not be
      present
<221> NAME/KEY: MISC_FEATURE
<222> LOCATION: (62)..(62)
<223> OTHER INFORMATION: X = Val, Leu, Ile or Nle and may or may not be
      present
<221> NAME/KEY: MISC_FEATURE
<222> LOCATION: (63)..(63)
<223> OTHER INFORMATION: X = Val, Leu, Ile or Nle and may or may not be
      present
<221> NAME/KEY: MISC_FEATURE
<222> LOCATION: (64)..(64)
<223> OTHER INFORMATION: X = Val, Leu, Ile or Nle and may or may not be
      present
<221> NAME/KEY: MISC_FEATURE
<222> LOCATION: (65)..(65)
<223> OTHER INFORMATION: X = Val, Leu, Ile or Nle and may or may not be
      present
<221> NAME/KEY: MISC_FEATURE
<222> LOCATION: (66)..(66)
<223> OTHER INFORMATION: X = Val, Leu, Ile or Nle and may or may not be
      present
<221> NAME/KEY: MISC_FEATURE
<222> LOCATION: (67)..(67)
<223> OTHER INFORMATION: X = Val, Leu, Ile or Nle and may or may not be
      present
<221> NAME/KEY: MISC_FEATURE
<222> LOCATION: (68)..(68)
<223> OTHER INFORMATION: X = Val, Leu, Ile or Nle and may or may not be
      present
<221> NAME/KEY: MISC_FEATURE
<222> LOCATION: (69)..(69)
<223> OTHER INFORMATION: X = Val, Leu, Ile or Nle and may or may not be
      present
<221> NAME/KEY: MISC_FEATURE
<222> LOCATION: (70)..(70)
<223> OTHER INFORMATION: X = Val, Leu, Ile or Nle and may or may not be
      present
<221> NAME/KEY: MISC_FEATURE
<222> LOCATION: (71)..(71)
<223> OTHER INFORMATION: X = Val, Leu, Ile or Nle and may or may not be
      present
<221> NAME/KEY: MISC_FEATURE
<222> LOCATION: (72)..(72)
<223> OTHER INFORMATION: X = Val, Leu, Ile or Nle and may or may not be
      present
<221> NAME/KEY: MISC_FEATURE
```

-continued

```
<222> LOCATION: (73)..(73)
<223> OTHER INFORMATION: X = Val, Leu, Ile or Nle and may or may not be
      present
<221> NAME/KEY: MISC_FEATURE
<222> LOCATION: (74)..(74)
<223> OTHER INFORMATION: X = Val, Leu, Ile or Nle and may or may not be
      present
<221> NAME/KEY: MISC_FEATURE
<222> LOCATION: (76)..(76)
<223> OTHER INFORMATION: X = Val, Leu, Ile or Nle and may or may not be
      present
<221> NAME/KEY: MISC_FEATURE
<222> LOCATION: (77)..(77)
<223> OTHER INFORMATION: X = Val, Leu, Ile or Nle and may or may not be
      present
<221> NAME/KEY: MISC_FEATURE
<222> LOCATION: (78)..(78)
<223> OTHER INFORMATION: X = Val, Leu, Ile or Nle and may or may not be
      present
<221> NAME/KEY: MISC_FEATURE
<222> LOCATION: (79)..(79)
<223> OTHER INFORMATION: X = Val, Leu, Ile or Nle and may or may not be
      present
<221> NAME/KEY: MISC_FEATURE
<222> LOCATION: (80)..(80)
<223> OTHER INFORMATION: X = Val, Leu, Ile or Nle and may or may not be
      present
<221> NAME/KEY: MISC_FEATURE
<222> LOCATION: (81)..(81)
<223> OTHER INFORMATION: X = Val, Leu, Ile or Nle and may or may not be
      present
<221> NAME/KEY: MISC_FEATURE
<222> LOCATION: (82)..(82)
<223> OTHER INFORMATION: X = Val, Leu, Ile or Nle and may or may not be
      present
<221> NAME/KEY: MISC_FEATURE
<222> LOCATION: (83)..(83)
<223> OTHER INFORMATION: X = Val, Leu, Ile or Nle and may or may not be
      present
<221> NAME/KEY: MISC_FEATURE
<222> LOCATION: (84)..(84)
<223> OTHER INFORMATION: X = Val, Leu, Ile or Nle and may or may not be
      present
<221> NAME/KEY: MISC_FEATURE
<222> LOCATION: (85)..(85)
<223> OTHER INFORMATION: X = Val, Leu, Ile or Nle and may or may not be
      present
<221> NAME/KEY: MISC_FEATURE
<222> LOCATION: (86)..(86)
<223> OTHER INFORMATION: X = Val, Leu, Ile or Nle and may or may not be
      present
<221> NAME/KEY: MISC_FEATURE
<222> LOCATION: (87)..(87)
<223> OTHER INFORMATION: X = Val, Leu, Ile or Nle and may or may not be
      present
<221> NAME/KEY: MISC_FEATURE
<222> LOCATION: (88)..(88)
<223> OTHER INFORMATION: X = Val, Leu, Ile or Nle and may or may not be
      present
<221> NAME/KEY: MISC_FEATURE
<222> LOCATION: (89)..(89)
<223> OTHER INFORMATION: X = Val, Leu, Ile or Nle and may or may not be
      present
<221> NAME/KEY: MISC_FEATURE
<222> LOCATION: (90)..(90)
<223> OTHER INFORMATION: X = Val, Leu, Ile or Nle and may or may not be
      present
<221> NAME/KEY: MISC_FEATURE
<222> LOCATION: (91)..(91)
<223> OTHER INFORMATION: X = Val, Leu, Ile or Nle and may or may not be
      present
<221> NAME/KEY: MISC_FEATURE
<222> LOCATION: (92)..(92)
<223> OTHER INFORMATION: X = Val, Leu, Ile or Nle and may or may not be
      present
<221> NAME/KEY: MISC_FEATURE
<222> LOCATION: (93)..(93)
<223> OTHER INFORMATION: X = Val, Leu, Ile or Nle and may or may not be
      present
```

```
<221> NAME/KEY: MISC_FEATURE
<222> LOCATION: (94)..(94)
<223> OTHER INFORMATION: X = Val, Leu, Cys, Ile or Nle and may or may
      not be present
<221> NAME/KEY: MISC_FEATURE
<222> LOCATION: (95)..(95)
<223> OTHER INFORMATION: X = Val, Leu, Ile or Nle and may or may not be
      present
<221> NAME/KEY: MISC_FEATURE
<222> LOCATION: (33)..(33)
<223> OTHER INFORMATION: X = Ornithine, Lys, Ile, Trp, Phe, Tyr, Gln, or
      Asn and may or may not be present
<221> NAME/KEY: MISC_FEATURE
<222> LOCATION: (53)..(53)
<223> OTHER INFORMATION: X = Ornithine, Lys, Ile, Trp, Phe, Tyr, Gln, or
      Asn and may or may not be present
<221> NAME/KEY: MISC_FEATURE
<222> LOCATION: (75)..(75)
<223> OTHER INFORMATION: X = Ornithine, Lys, Ile, Trp, Phe, Tyr, Gln, or
      Asn and may or may not be present
<221> NAME/KEY: MISC_FEATURE
<222> LOCATION: (75)..(75)
<223> OTHER INFORMATION: X = Ornithine, Lys, Ile, Trp, Phe, Tyr, Gln, or
      Asn and may or may not be present

<400> SEQUENCE: 1

Xaa Xaa Ile Pro Xaa Xaa Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Gly Ala
            85                  90                  95

Leu Leu Met Gly Leu
            100

<210> SEQ ID NO 2
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (13)..(13)
<223> OTHER INFORMATION: X = Lys or Phe
<221> NAME/KEY: MISC_FEATURE
<222> LOCATION: (18)..(18)
<223> OTHER INFORMATION: X = Lys or Phe
<221> NAME/KEY: MISC_FEATURE
<222> LOCATION: (23)..(23)
<223> OTHER INFORMATION: X = Lys or Phe
<221> NAME/KEY: MISC_FEATURE
<222> LOCATION: (28)..(28)
<223> OTHER INFORMATION: X = Lys or Phe
<221> NAME/KEY: MISC_FEATURE
<222> LOCATION: (14)..(14)
<223> OTHER INFORMATION: X = Ley, Ile, or Nle
<221> NAME/KEY: MISC_FEATURE
<222> LOCATION: (15)..(15)
<223> OTHER INFORMATION: X = Ley, Ile, or Nle
<221> NAME/KEY: MISC_FEATURE
<222> LOCATION: (16)..(16)
<223> OTHER INFORMATION: X = Ley, Ile, or Nle
<221> NAME/KEY: MISC_FEATURE
<222> LOCATION: (17)..(17)
<223> OTHER INFORMATION: X = Ley, Ile, or Nle
```

```
<221> NAME/KEY: MISC_FEATURE
<222> LOCATION: (19)..(19)
<223> OTHER INFORMATION: X = Ley, Ile, or Nle
<221> NAME/KEY: MISC_FEATURE
<222> LOCATION: (20)..(20)
<223> OTHER INFORMATION: X = Ley, Ile, or Nle
<221> NAME/KEY: MISC_FEATURE
<222> LOCATION: (21)..(21)
<223> OTHER INFORMATION: X = Ley, Ile, or Nle
<221> NAME/KEY: MISC_FEATURE
<222> LOCATION: (22)..(22)
<223> OTHER INFORMATION: X = Ley, Ile, or Nle
<221> NAME/KEY: MISC_FEATURE
<222> LOCATION: (24)..(24)
<223> OTHER INFORMATION: X = Ley, Ile, or Nle
<221> NAME/KEY: MISC_FEATURE
<222> LOCATION: (25)..(25)
<223> OTHER INFORMATION: X = Ley, Ile, or Nle
<221> NAME/KEY: MISC_FEATURE
<222> LOCATION: (26)..(26)
<223> OTHER INFORMATION: X = Ley, Ile, or Nle
<221> NAME/KEY: MISC_FEATURE
<222> LOCATION: (27)..(27)
<223> OTHER INFORMATION: X = Ley, Ile, or Nle
<221> NAME/KEY: MISC_FEATURE
<222> LOCATION: (29)..(29)
<223> OTHER INFORMATION: X = Ley, Ile, or Nle

<400> SEQUENCE: 2

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Gly Ala Leu Leu
            20                  25                  30

Met Gly Leu
        35

<210> SEQ ID NO 3
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (18)..(18)
<223> OTHER INFORMATION: X = Lys or Phe
<221> NAME/KEY: MISC_FEATURE
<222> LOCATION: (24)..(24)
<223> OTHER INFORMATION: X = Lys or Phe
<221> NAME/KEY: MISC_FEATURE
<222> LOCATION: (13)..(13)
<223> OTHER INFORMATION: X = Leu, Ile, or Nle
<221> NAME/KEY: MISC_FEATURE
<222> LOCATION: (14)..(14)
<223> OTHER INFORMATION: X = Leu, Ile, or Nle
<221> NAME/KEY: MISC_FEATURE
<222> LOCATION: (15)..(15)
<223> OTHER INFORMATION: X = Leu, Ile, or Nle
<221> NAME/KEY: MISC_FEATURE
<222> LOCATION: (16)..(16)
<223> OTHER INFORMATION: X = Leu, Ile, or Nle
<221> NAME/KEY: MISC_FEATURE
<222> LOCATION: (17)..(17)
<223> OTHER INFORMATION: X = Leu, Ile, or Nle
<221> NAME/KEY: MISC_FEATURE
<222> LOCATION: (19)..(19)
<223> OTHER INFORMATION: X = Leu, Ile, or Nle
<221> NAME/KEY: MISC_FEATURE
<222> LOCATION: (20)..(20)
<223> OTHER INFORMATION: X = Leu, Ile, or Nle
<221> NAME/KEY: MISC_FEATURE
<222> LOCATION: (21)..(21)
<223> OTHER INFORMATION: X = Leu, Ile, or Nle
<221> NAME/KEY: MISC_FEATURE
<222> LOCATION: (22)..(22)
<223> OTHER INFORMATION: X = Leu, Ile, or Nle
```

```
<221> NAME/KEY: MISC_FEATURE
<222> LOCATION: (23)..(23)
<223> OTHER INFORMATION: X = Leu, Ile, or Nle
<221> NAME/KEY: MISC_FEATURE
<222> LOCATION: (25)..(25)
<223> OTHER INFORMATION: X = Leu, Ile, or Nle
<221> NAME/KEY: MISC_FEATURE
<222> LOCATION: (26)..(26)
<223> OTHER INFORMATION: X = Leu, Ile, or Nle
<221> NAME/KEY: MISC_FEATURE
<222> LOCATION: (27)..(27)
<223> OTHER INFORMATION: X = Leu, Ile, or Nle
<221> NAME/KEY: MISC_FEATURE
<222> LOCATION: (28)..(28)
<223> OTHER INFORMATION: X = Leu, Ile, or Nle

<400> SEQUENCE: 3

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Gly Ala Leu Leu
            20                  25                  30

Met Gly Leu
        35

<210> SEQ ID NO 4
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (17)..(17)
<223> OTHER INFORMATION: X = Lys or Phe
<221> NAME/KEY: MISC_FEATURE
<222> LOCATION: (13)..(13)
<223> OTHER INFORMATION: X = Leu, Ile, or Nle
<221> NAME/KEY: MISC_FEATURE
<222> LOCATION: (14)..(14)
<223> OTHER INFORMATION: X = Leu, Ile, or Nle
<221> NAME/KEY: MISC_FEATURE
<222> LOCATION: (15)..(15)
<223> OTHER INFORMATION: X = Leu, Ile, or Nle
<221> NAME/KEY: MISC_FEATURE
<222> LOCATION: (16)..(16)
<223> OTHER INFORMATION: X = Leu, Ile, or Nle
<221> NAME/KEY: MISC_FEATURE
<222> LOCATION: (18)..(18)
<223> OTHER INFORMATION: X = Leu, Ile, or Nle
<221> NAME/KEY: MISC_FEATURE
<222> LOCATION: (19)..(19)
<223> OTHER INFORMATION: X = Leu, Ile, or Nle
<221> NAME/KEY: MISC_FEATURE
<222> LOCATION: (20)..(20)
<223> OTHER INFORMATION: X = Leu, Ile, or Nle
<221> NAME/KEY: MISC_FEATURE
<222> LOCATION: (21)..(21)
<223> OTHER INFORMATION: X = Leu, Ile, or Nle
<221> NAME/KEY: MISC_FEATURE
<222> LOCATION: (22)..(22)
<223> OTHER INFORMATION: X = Leu, Ile, or Nle
<221> NAME/KEY: MISC_FEATURE
<222> LOCATION: (23)..(23)
<223> OTHER INFORMATION: X = Leu, Ile, or Nle
<221> NAME/KEY: MISC_FEATURE
<222> LOCATION: (24)..(24)
<223> OTHER INFORMATION: X = Leu, Ile, or Nle
<221> NAME/KEY: MISC_FEATURE
<222> LOCATION: (25)..(25)
<223> OTHER INFORMATION: X = Leu, Ile, or Nle
<221> NAME/KEY: MISC_FEATURE
<222> LOCATION: (26)..(26)
<223> OTHER INFORMATION: X = Leu, Ile, or Nle
<221> NAME/KEY: MISC_FEATURE
<222> LOCATION: (27)..(27)
<223> OTHER INFORMATION: X = Leu, Ile, or Nle
```

<221> NAME/KEY: MISC_FEATURE
<222> LOCATION: (28)..(28)
<223> OTHER INFORMATION: X = Leu, Ile, or Nle

<400> SEQUENCE: 4

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Gly Ala Leu Leu
            20                  25                  30

Met Gly Leu
        35

<210> SEQ ID NO 5
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (21)..(21)
<223> OTHER INFORMATION: X = Lys or Phe
<221> NAME/KEY: MISC_FEATURE
<222> LOCATION: (13)..(13)
<223> OTHER INFORMATION: X = Lue, Ile, Nle
<221> NAME/KEY: MISC_FEATURE
<222> LOCATION: (14)..(14)
<223> OTHER INFORMATION: X = Lue, Ile, Nle
<221> NAME/KEY: MISC_FEATURE
<222> LOCATION: (15)..(15)
<223> OTHER INFORMATION: X = Lue, Ile, Nle
<221> NAME/KEY: MISC_FEATURE
<222> LOCATION: (16)..(16)
<223> OTHER INFORMATION: X = Lue, Ile, Nle
<221> NAME/KEY: MISC_FEATURE
<222> LOCATION: (17)..(17)
<223> OTHER INFORMATION: X = Lue, Ile, Nle
<221> NAME/KEY: MISC_FEATURE
<222> LOCATION: (18)..(18)
<223> OTHER INFORMATION: X = Lue, Ile, Nle
<221> NAME/KEY: MISC_FEATURE
<222> LOCATION: (19)..(19)
<223> OTHER INFORMATION: X = Lue, Ile, Nle
<221> NAME/KEY: MISC_FEATURE
<222> LOCATION: (20)..(20)
<223> OTHER INFORMATION: X = Lue, Ile, Nle
<221> NAME/KEY: MISC_FEATURE
<222> LOCATION: (22)..(22)
<223> OTHER INFORMATION: X = Lue, Ile, Nle
<221> NAME/KEY: MISC_FEATURE
<222> LOCATION: (23)..(23)
<223> OTHER INFORMATION: X = Lue, Ile, Nle
<221> NAME/KEY: MISC_FEATURE
<222> LOCATION: (24)..(24)
<223> OTHER INFORMATION: X = Lue, Ile, Nle
<221> NAME/KEY: MISC_FEATURE
<222> LOCATION: (25)..(25)
<223> OTHER INFORMATION: X = Lue, Ile, Nle
<221> NAME/KEY: MISC_FEATURE
<222> LOCATION: (26)..(26)
<223> OTHER INFORMATION: X = Lue, Ile, Nle
<221> NAME/KEY: MISC_FEATURE
<222> LOCATION: (27)..(27)
<223> OTHER INFORMATION: X = Lue, Ile, Nle
<221> NAME/KEY: MISC_FEATURE
<222> LOCATION: (28)..(28)
<223> OTHER INFORMATION: X = Lue, Ile, Nle

<400> SEQUENCE: 5

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Gly Ala Leu Leu
            20                  25                  30

Met Gly Leu
        35

<210> SEQ ID NO 6
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (24)..(24)
<223> OTHER INFORMATION: X = Lys or Phe
<221> NAME/KEY: MISC_FEATURE
<222> LOCATION: (13)..(13)
<223> OTHER INFORMATION: X = Leu, Ile, or Nle
<221> NAME/KEY: MISC_FEATURE
<222> LOCATION: (14)..(14)
<223> OTHER INFORMATION: X = Leu, Ile, or Nle
<221> NAME/KEY: MISC_FEATURE
<222> LOCATION: (15)..(15)
<223> OTHER INFORMATION: X = Leu, Ile, or Nle
<221> NAME/KEY: MISC_FEATURE
<222> LOCATION: (16)..(16)
<223> OTHER INFORMATION: X = Leu, Ile, or Nle
<221> NAME/KEY: MISC_FEATURE
<222> LOCATION: (17)..(17)
<223> OTHER INFORMATION: X = Leu, Ile, or Nle
<221> NAME/KEY: MISC_FEATURE
<222> LOCATION: (18)..(18)
<223> OTHER INFORMATION: X = Leu, Ile, or Nle
<221> NAME/KEY: MISC_FEATURE
<222> LOCATION: (19)..(19)
<223> OTHER INFORMATION: X = Leu, Ile, or Nle
<221> NAME/KEY: MISC_FEATURE
<222> LOCATION: (20)..(20)
<223> OTHER INFORMATION: X = Leu, Ile, or Nle
<221> NAME/KEY: MISC_FEATURE
<222> LOCATION: (21)..(21)
<223> OTHER INFORMATION: X = Leu, Ile, or Nle
<221> NAME/KEY: MISC_FEATURE
<222> LOCATION: (22)..(22)
<223> OTHER INFORMATION: X = Leu, Ile, or Nle
<221> NAME/KEY: MISC_FEATURE
<222> LOCATION: (23)..(23)
<223> OTHER INFORMATION: X = Leu, Ile, or Nle
<221> NAME/KEY: MISC_FEATURE
<222> LOCATION: (25)..(25)
<223> OTHER INFORMATION: X = Leu, Ile, or Nle
<221> NAME/KEY: MISC_FEATURE
<222> LOCATION: (26)..(26)
<223> OTHER INFORMATION: X = Leu, Ile, or Nle
<221> NAME/KEY: MISC_FEATURE
<222> LOCATION: (27)..(27)
<223> OTHER INFORMATION: X = Leu, Ile, or Nle
<221> NAME/KEY: MISC_FEATURE
<222> LOCATION: (28)..(28)
<223> OTHER INFORMATION: X = Leu, Ile, or Nle

<400> SEQUENCE: 6

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Gly Ala Leu Leu
            20                  25                  30

Met Gly Leu
        35

<210> SEQ ID NO 7
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Phe Gly Ile Pro Ser Ser Pro Val His Leu Lys Arg Leu Leu Ile Leu
1               5                   10                  15

Lys Leu Leu Leu Leu Lys Ile Leu Leu Lys Leu Gly Ala Leu Leu
            20                  25                  30

Met Gly Leu
        35

<210> SEQ ID NO 8
<211> LENGTH: 35
<212> TYPE: PRT
<213> ORGANISM: ARTIFICIAL SEQUENCE
<220> FEATURE:
<223> OTHER INFORMATION: SYNTHEIC PEPTIDE

<400> SEQUENCE: 8

Phe Gly Ile Pro Ser Ser Pro Val His Leu Lys Arg Leu Leu Ile Leu
1               5                   10                  15

Leu Lys Leu Leu Leu Leu Ile Lys Leu Leu Ile Leu Gly Ala Leu Leu
            20                  25                  30

Met Gly Leu
        35

<210> SEQ ID NO 9
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

Phe Gly Ile Pro Ser Ser Pro Val His Leu Lys Arg Leu Leu Ile Leu
1               5                   10                  15

Lys Leu Leu Leu Leu Leu Ile Leu Leu Ile Leu Gly Ala Leu Leu
            20                  25                  30

Met Gly Leu
        35

<210> SEQ ID NO 10
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 10

Phe Gly Ile Pro Ser Ser Pro Val His Leu Lys Arg Leu Leu Ile Leu
1               5                   10                  15

Leu Leu Leu Leu Lys Leu Ile Leu Leu Ile Leu Gly Ala Leu Leu
            20                  25                  30

Met Gly Leu
        35

<210> SEQ ID NO 11
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

Phe Gly Ile Pro Ser Ser Pro Val His Leu Lys Arg Leu Leu Ile Leu
1               5                   10                  15

```
Leu Leu Leu Leu Leu Leu Ile Lys Leu Leu Ile Leu Gly Ala Leu Leu
            20                  25                  30

Met Gly Leu
        35

<210> SEQ ID NO 12
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 12

Phe Gly Ile Pro Ser Ser Pro Val His Leu Lys Arg Leu Leu Ile Leu
1               5                   10                  15

Phe Leu Leu Leu Leu Phe Ile Leu Leu Leu Phe Leu Gly Ala Leu Leu
            20                  25                  30

Met Gly Leu
        35

<210> SEQ ID NO 13
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 13

Phe Gly Ile Pro Cys Cys Pro Val His Leu Lys Arg Leu Leu Ile Val
1               5                   10                  15

Val Val Val Val Val Leu Ile Val Val Val Ile Val Gly Gln Leu Leu
            20                  25                  30

Met Gly Leu
        35

<210> SEQ ID NO 14
<211> LENGTH: 34
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 14

Phe Gly Ile Pro Ser Ser Pro Val Leu Lys Arg Leu Leu Ile Leu Leu
1               5                   10                  15

Leu Leu Leu Leu Leu Ile Leu Leu Leu Ile Leu Gly Ala Leu Leu Met
            20                  25                  30

Gly Leu
```